United States Patent [19]

Nelson

[11] 4,148,879

[45] Apr. 10, 1979

[54] INHIBITION OF PLATELET AGGREGATION WITH SELECTED PHOSPHONIC AND PHOSPHINIC ACID ESTERS

[75] Inventor: Eric L. Nelson, Santa Ana, Calif.

[73] Assignee: Nelson Research & Development Company, Irvine, Calif.

[21] Appl. No.: 864,017

[22] Filed: Dec. 23, 1977

[51] Int. Cl.$^2$ .................. A61K 35/14; A61K 31/685; A61K 31/66
[52] U.S. Cl. ..................................... 424/101; 424/199; 424/210; 424/211; 424/214; 424/217; 424/218; 424/219; 424/220; 424/222; 424/224; 195/1.8
[58] Field of Search ............... 424/199, 210, 211, 214, 424/217, 218, 219, 220, 222, 224, 101

[56] References Cited

U.S. PATENT DOCUMENTS 3,984,501  10/1976  Rajadhyaksha et al. ........ 424/210 X
4,016,223   4/1977  Rajadhyaksha et al. ........ 424/210 X Primary Examiner—Frederick E. Waddell
Attorney, Agent, or Firm—Martin A. Voet

[57] ABSTRACT

A process for inhibiting platelet aggregation or thrombus formation by the addition of a member selected from the group consisting of a compound of the formula:

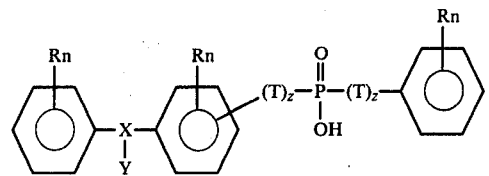

wherein X is an alkyl or alkenyl chain having 2–8 carbon atoms, one of which carbon atoms may be in the form of a carbonyl group, Y is H, alkyl, dialkylaminoethyl, aryl, aralkyl or aryl and aralkyl substituted with one or more R, and R is H, lower alkyl, lower alkoxy, halogen, $CF_3$, $NO_2$, OH, CN, $COOR_1$,

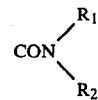

$NHCOR_1$, $NR_1R_2$ or

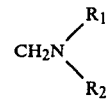

where $R_1$ and $R_2$ are each selected from the group consisting of H and lower alkyl; R, $R_1$ and $R_2$ being the same or different, T is selected from the group consisting of O, NH, S and $CH_2$ with the proviso that only one T is O, Z is 0 or 1 and n is 0–5; and pharmaceutically acceptable salts thereof, to in vivo and in vitro platelet systems.

5 Claims, No Drawings

INHIBITION OF PLATELET AGGREGATION WITH SELECTED PHOSPHONIC AND PHOSPHINIC ACID ESTERS

BACKGROUND OF THE INVENTION

1. Field of the Invention

The present invention relates to the prevention of platelet aggregation or thrombus formation by the use of a compound as described herein.

2. Background of the Prior Art

The compounds disclosed herein are old compounds known in the art, e.g., U.S. Pat. No. 3,984,501.

SUMMARY OF THE INVENTION

There has now been discovered a process for inhibiting platelet aggregation or thrombus formation by the addition of a member selected from the group consisting of a compound of the formula:

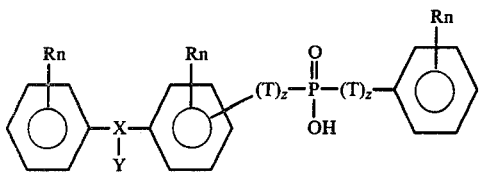

wherein X is an alkyl or alkenyl chain having 2-8 carbon atoms, one of which carbon atoms may be in the form of a carbonyl group, Y is H, alkyl, dialkylaminoethyl, aryl, aralkyl or aryl and aralkyl substituted with one or more R, and R is H, lower alkyl, lower alkoxy, halogen, $CF_3$, $NO_2$, OH, CN, $COOR_1$,

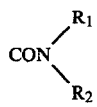

$NHCOR_1$, $NR_1R_2$ or

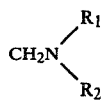

where $R_1$ and $R_2$ are each selected from the group consisting of H and lower alkyl; R, $R_1$ and $R_2$ being the same or different, T is selected from the group consisting of O, N, H, S and $CH_2$ with the proviso that only one T is 0, Z is 0, or 1 and n is 0-5; and pharmaceutically acceptable salts thereof, to in vivo and in vitro platelet systems. In vitro systems include whole blood as kept in blood banks, whole blood as used in heart-lung machines and platelet-rich concentrates. In vivo systems include human or animal bodies.

Preferred active compounds include those compounds of the foregoing structural formula wherein X is an alkyl or alkenyl chain having 3 carbon atoms, with or without a carbonyl group, R is H, Y is benzyl or phenyl substituted with Cl or Br, preferably in the para position and T is 0 and $CH_2$ and Z is 1.

DETAILED DESCRIPTION

For in vivo applications the compositions of the present invention are presented for administration to humans and animals in unit dosage forms, such as tablets, capsules, pills, powders, granules, sterile parenteral solutions or suspensions, and oil-in-water and water-in-oil emulsions containing suitable quantities of one of the active compounds described herein.

For oral administration either solid or fluid unit dosage forms can be prepared. For preparing solid compositions such as tablets, a suitable compound as disclosed herein is mixed with conventional ingredients such as talc, magnesium stearate, dicalcium phosphate, magnesium aluminum silicate, calcium sulfate, starch, lactose, acacia methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydro-alcoholic (ethanol) vehicle with suitable sweeteners such as sugar and saccharin, together with an aromatic flavoring agent.

Suspensions can be prepared with a syrup vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filler sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions are prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

For in vitro applications, aqueous solutions are prepared by dissolving the compound in water and adding salt to provide an isotonic solution and buffering to a pH compatible with blood.

Advantageously the composition prepared for parenteral administration can be used when prepared omitting the local anesthetic.

The dosage for humans and animals depends on the blood volume and condition of the subject. A dosage schedule of from about 0.1 to about 100 mg. per dose administered 1 to 3 times daily is effective for reducing platelet aggregation in the subject. Expressed in terms of weight, the dose can be from 0.001 to 1.5 mg/kg/day. The preferred dose is 1 to 10 mg orally 1 to 3 times a day for an adult human.

For in vitro, dosage is from 0.01 to 50 micrograms/ml of whole blood.

The compounds disclosed herein are depicted in the protonated or acid form, however, for the purposes of the instant invention the proton can be replaced by any pharmacological acceptable anion. Typical salts are disclosed in the prior art and can be for example those of alkali metals and alkaline earth bases, such as the sodium potassium, calcium and magnesium salts; those of ammonia or a basic amine such as mono-, and triethyl amines, benzylamine, heterocyclic amines such as piperidine and morpholine, and amines containing water-solubilizing or hydrophilic groups such as triethanolamine and phenylmonoethanolamine are disclosed in U.S. Pat. No. 3,296,091. Carboxylate esters such as methyl, ethyl, cyclohexyl and the like having no more than eight carbon atoms are formed by the usual methods, e.g., reaction with diazomethane or similar diazohydrocarbons as in U.S. Pat. No. 3,296,091.

The addition of compounds disclosed herein to whole blood provide in vitro applications of the invention such as in the storage of whole blood in blood banks, and whole blood to be used in heart-lung machines. Additionally, whole blood containing a compound can be circulated through organs, e.g., heart and kidneys, which have been removed from a cadaver and prior to transplant.

The compounds can also be used for the preparation of stable platelet-rich plasma concentrates in the same manner as the prostaglandins as disclosed in U.S. Pat. No. 3,629,071 and Science. Vol. 175, pp. 526–542 (Feb. 4, 1972).

In vivo applications are the administration to humans and animals to prevent clot formation in situations such as following surgery to prevent postoperative thrombosis; in geriatric patients to prevent transient cerebral ischemic attacks and long-term prophylaxis following myocardial infarcts and strokes.

EXAMPLE 1

A lot of 10,000 tablets, each containing 0.1 mg of sodium p-benzyl-4-[1-oxo-2-(4-chlorobenzyl)-3-phenylpropyl] phenyl phosphate is prepared from the following types and amounts of ingredients:

| | |
|---|---|
| Sodium p-benzyl-4-[1-oxo-2-(4-chlorobenzyl)-3-phenylpropyl] phenyl phosphate | 1 Gm |
| Dicalcium phosphate | 1,500 Gm |
| Methylcellulose, U.S.P. (15 cps.) | 60 Gm |
| Talc | 150 Gm |
| Corn starch | 200 Gm |
| Calcium stearate | 12 Gm |

The dicalcium phosphate is mixed well, granulated with 7.5 percent solution of methylcellulose in water, passed through a No. 8 screen and dried carefully. The dried granules are passed through a No. 12 screen, mixed thoroughly with the talc, starch and magnesium stearate, and compressed into tablets.

These tablets are useful in preventing thrombus formation at a dose of 1 tablet every four hours following surgery.

EXAMPLE 2

One thousand two-piece hard gelatin capsules, each containing 100 mg of sodium p-benzyl-4-[1-oxo-2-(4-chlorobenzyl)-3-phenylpropyl] phenyl phosphate are prepared from the following types and amounts of ingredients:

| | |
|---|---|
| Sodium p-benzyl-4-[1-oxo-2-(4-chlorobenzyl)-3-phenylpropyl] phenyl phosphate | 100 Gm |
| Talc | 100 Gm |
| Magnesium stearate | 10 GM |

These ingredients are mixed well and filled into capsules of the proper size.

Capsules so prepared are useful in preventing further coronary infarcts at a dose of 1 capsule daily to a patient recovering from a coronary infarct.

EXAMPLE 3

One thousand tablets, each containing 100 mg of sodium p-benzyl-4-[1-oxo-2-(4-chlorobenzyl)-3-phenylpropyl] phenyl phosphate is prepared from the following types and amounts of ingredients:

| | |
|---|---|
| Sodium p-benzyl-4-[1-oxo-2-(4-chlorobenzyl)-3-phenylpropyl] phenyl phosphate | 100 Gm |
| Microcrystalline cellulose NF | 120 Gm |
| Starch | 16 Gm |
| Magnesium stearate powder | 4 Gm |

These ingredients are screened and blended together and pressed into 240 mg tablets.

The tablets are useful to protect against transient cerebral ischemic attacks at a dose of 1 tablet daily.

EXAMPLE 4

A sterile preparation suitable for intramuscular injection and consisting 1 mg of sodium p-benzyl-4-[1-oxo-2-(4-chlorobenzyl)-3-phenylpropyl] phenyl phosphate in each milliliter is prepared from the following ingredients:

| | | |
|---|---|---|
| Sodium p-benzyl-4-[1-oxo-2-(4-chlorobenzyl)-3-phenylpropyl] phenyl phosphate | 1 | Gm |
| Benzyl benzoate | 200 | ml |
| Methylparaben | 1.5 | Gm |
| Propylparaben | 0.5 | Gm |
| Cottonseed oil q.s. | 1,000 | ml |

One milliliter of this sterile preparation is injected for prophylactic treatment prior to surgery.

I claim:

1. A process for inhibiting platelet aggregation in in vitro platelet systems comprising the addition of an effective amount of a compound of the formula:

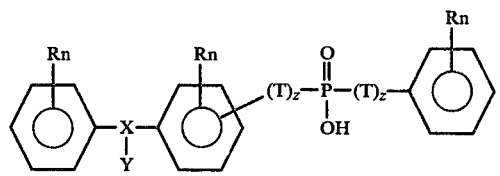

wherein X is an alkyl or alkenyl chain having 2–8 carbon atoms, one of which carbon atoms may be in the form of a carbonyl group, Y is H, alkyl, dialkylaminoethyl, aryl, aralkyl or aryl and aralkyl substituted with one or more R, and R is H, lower alkyl, lower alkoxy, halogen, $CF_3$, $NO_2$, OH, CN, $COOR_1$,

NHCOR$_1$, NR$_1$R$_2$ or

where R$_1$ and R$_2$ are each selected from the group consisting of H and lower alkyl; R, R$_1$ and R$_2$ being the same or different, T is selected from the group consisting of O, N, H, S and CH$_2$, with the proviso that only one T is O; Z is 0 or 1 and n is 0–5; and pharmaceutically acceptable salts thereof, to in vitro platelet systems.

2. The process of claim 1 wherein the amount of the compound added is from about 0.01 to 50 micrograms per ml of whole blood.

3. The process of claim 1 wherein the compound added is selected from the group consisting of p-benzyl-4-[1-oxo-2-(4-chlorobenzyl)-3-phenylpropyl] phenyl phosphonic acid and pharmaceutically acceptable salts thereof.

4. A process of prophylactic treatment to prevent clot formation in humans and animals comprising the administration to a human or animal of an effective amount of a compound of the formula:

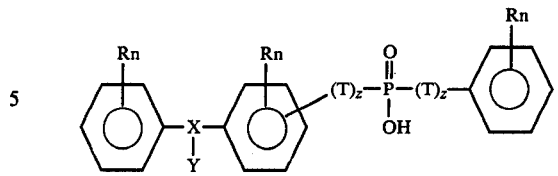

wherein X is an alkyl or alkenyl chain having 2–8 carbon atoms, one of which carbon atoms may be in the form of a carbonyl group, Y is H, alkyl, dialkylaminoethyl, aryl, aralkyl or aryl and aralkyl substituted with one or more R, and R is H, lower alkyl, lower alkoxy, halogen, CF$_3$, NO$_2$, OH, CN, COOR$_1$,

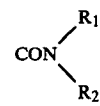

NHCOR$_1$, NR$_1$R$_2$ or

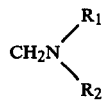

where R$_1$ and R$_2$ are each selected from the group consisting of H and lower alkyl; R, R$_1$ and R$_2$ being the same or different, T is selected from the group consisting of O, N, H, S and CH$_2$ with the proviso that only one T is O; Z is 0 or 1 and n is 0–5; and pharmaceutically acceptable salts thereof.

5. The process of claim 4 wherein the compound added is selected from the group consisting of p-benzyl-4-[1-oxo-2-(4-chlorobenzyl)-3-phenyl-propyl] phenyl phosphonic acid and pharmaceutically acceptable salts thereof.

* * * * *